United States Patent [19]

Loria et al.

[11] Patent Number: 5,077,284

[45] Date of Patent: Dec. 31, 1991

[54] USE OF DEHYDROEPIANDROSTERONE TO IMPROVE IMMUNE RESPONSE

[76] Inventors: Roger M. Loria; William Regelson, both of P.O. Box 678, Richmond, Va. 23298

[21] Appl. No.: 291,969

[22] Filed: Dec. 30, 1988

[51] Int. Cl.$^5$ .................. A01N 45/00; A61K 31/565; A61K 9/08; A61K 9/48

[52] U.S. Cl. ................................ 514/171; 514/169; 514/170; 514/885; 514/937; 424/434; 424/451; 424/464

[58] Field of Search ............... 514/169, 170, 171, 885, 514/937; 424/434, 451, 464

[56] References Cited

U.S. PATENT DOCUMENTS 4,628,052 12/1986 Peat ........................................ 514/171
4,666,898 5/1987 Coleman et al. ..................... 514/177

FOREIGN PATENT DOCUMENTS

3812595A1 10/1988 Fed. Rep. of Germany .

OTHER PUBLICATIONS

The Irish Business article entitled "AIDS", published Apr. 1988.
R. M. Loria et al., "Protection Against Acute Lethal Viral Infections with the Native Steroid Dehydroepiandrosterone (DHEA)", Journal of Medical Virology, 26:301–314 (1988).
The Anti-Aging News, Edited by Susan Ellis, OMNI Longevity, Oct. 1988.
The Richmond Times–Dispatch, Sunday, Mar. 17, 1988 article, "As Hormones Go, DHEA is a Puzzle for Scientists", by Beverly Orndorff.
The Chemical Week article, Dec. 10, 1986, "DHEA's Many Promises Move Toward Fulfillment".
The Annals New York Academy of Sciences article, "Hormonal Intervention: Buffer Hormones or State Dependency", Regelson et al., pp. 260–273.

*Primary Examiner*—Thurman K. Page
*Assistant Examiner*—Carlos Azpura
*Attorney, Agent, or Firm*—Glenna Hendricks

[57] ABSTRACT

The steroid hormone dehydroepiandrosterone (DHEA), when administered by feeding or by subcutaneous injection, significantly improves the host response to viral infection. Experimental animal data shows that, with infection (100,000 plaque forming units/animal) of a human coxsackievirus B4 strain, which causes mortality in about 90% of infected animals, mortality was reduced to 37% when animals were treated with DHEA. Moreover, DHEA induced an 80% elevation in the number of antibody forming cells, particularly in cells forming gamma globulin M (early antibodies), and gamma globulin G (secondary antibodies). This elevation in the number of antibody forming cells was evident only in DHEA treated and virus infected animals, but not in uninfected animals treated with DHEA or in infected animals not treated with DHEA. In virus infected and DHEA treated animals there was also an elevation in the number of monocyte cells, the particular white blood cell associated with a resistance to this infection. This elevation was not observed in hormone treated uninfected animals. This observation shows that DHEA can be used to up regulate the host immune response to virus infection, by increasing the number of antibody forming cells, elevating the number of white blood cells associated with resistance to virus infection and markedly reducing virus induced mortality. Virus (antigen) has to present in order to demonstrate the up regulation of immunity by the hormone.

7 Claims, 2 Drawing Sheets

USE OF DEHYDROEPIANDROSTERONE TO IMPROVE IMMUNE RESPONSE

BACKGROUND OF THE INVENTION

This invention relates to improving the response of the mammalian immune system and, more particularly, to the subcutaneous or oral administration of dehydroepiandrosterone as a human immune system up-regulator to protect against both DNA and RNA viral infections, such as coxsackievirus B4 (CVB4), herpes simplex type 2 (HSV2) and human immunodeficiency virus (HIV).

Virus infection, whether produced by retroviruses such as HIV, feline or Friend leukemia, is associated with prolonged immunosuppression, i.e., down regulation of the immune system. Other viruses, such as influenza or coxsackievirus have immunosuppressive effects of transient but significant clinical consequence.

The expression of virus, bacterial, fungal or parasitic disease is seen when immunosuppression provides the opportunity for infectious organisms to grow in the host. In this regard, it does not matter if the primary insult to immunity is viral, bacterial or the result of chemotherapy, radiation or severe stress.

In general, it has been thought that steroid hormones of adrenocortical origin, when administered at pharmacological doses, are immunosuppressive. T. R. Cupps and A. S. Fauci, Immunolo. Rev. 65, 133-155 (1982); H. N. Claman, Clin. Immunol. Allergy 4, 317-329 (1984); C. J. Grossman, Endocrine Reviews 5, 435-455 (1984); A. Goldien, in: Basic and Clinical Pharmacology, B. G. Katzung, ed. Third Edition, Norwalk, Conn., (Appleton & Lange 1987) pp. 449-460; and J. E. Parillo and A. S. Fauci, Annual Reviews of Pharmacology and Toxicology 19, 179-201 (1979).

Such immunosuppression is believed particularly evident with viral infections. E. D. Kilbourne and F. L. Horsfall, Proceedings: Society of Experimental Biology and Medicine 77, 135-138 (1951); B. G. Gatmaitan et al., J. Exp. Med. 131, 121-1136 (1970); and M. W. Rytel, J. Infect. Dis. 120. 379-382 (1969). For example, it has been shown that the administration of glucocorticoids results in higher viral tissue titers and increased symptomatology. D. L. Lynden and S. A. Huber, Cellular Immunol. 87, 462-472 (1984); E. S. Meek and B. Golden, in: Infectious Diseases, P. D. Hoeprich, ed. (Harper and Row Publ., New York 1972) pp. 1241-1242; B. I. Hollinger, in: Virology, B. N. Fields et al., eds. (New York, Raven Press 1985) pg. 1424; K. M. Johnson in: Virology, supra, pg. 1046; and D. L. Yirrell et al., Virol. 68, 2461-2464 (1987).

Dehydroepiandrosterone, also known as 3-beta-hydroxyandrost-5-en-17-one or dehydroiso-androsterone (referred to hereinafter as DHEA), is a 17-ketosteroid which is quantitatively one of the major adrenocortical steroid hormones present in the metabolism of humans and other mammals. M. E. Windholz, The Merck Index, Ninth Edition (1976); K. Diem and C. Lentner, Geigy Scientific Tables (1975); E. Barret-Connor et al., N.E.J.M. 315, 1519-1524 (1986). Although DHEA appears to serve as an intermediary in gonadal steroid synthesis, the primary physiological function of DHEA is unclear. It is known, however, that levels of this hormone begin to decline in the second decade of life reaching 5% of the original level in the elderly.

Clinically, DHEA has been used systemically and/or topically for psoriasis and has been used in the treatment of gout, hyperlipemia, and in post-coronary patients. W. Regelson et al., New York Academy of Sciences 518, 260-273 (1988). In animal models and in humans it has shown an antiobesity effect, and an anticarcinogenic action in animals. Comoare T. T. Yen et al., Lipids 12, 409 (1977); J. E. Nestler et al., J. Clinical Endocrinology and Metabolism 66, 57-61 (1988); articles by C. Lopez and B. T. Rouse, respectively, in: Immunobiology of Herpes Simplex Virus Infection; B. T. Rouse and C. Lopez, eds. (CRC Press, Boca Raton, Fla. (1984)) pp. 45-69, and 107-120, respectively; E. Henderson et al., Carcinogenesis 2, 683-686 (1981); and A. Schwartz in: Molecular Biology of Aging, A. D. Woodhead ed., Vol. 35 (Plenum Pub. Co., New York (1985)) pp. 181-191.

DHEA is still used clinically in Europe, in conjunction with estrogen as an agent to reverse menopausal systems and also has been used in the treatment of manic depression, schizophrenia, and Alzheimer's disease.

DHEA has also been studied clinically at 40 mg/kg/day in the treatment of advanced cancer and for its potential role in multiple sclerosis. Regelson, supra. Mild androgenic effects, hirsutism, and increased libido were the side effects observed. These side effects can be overcome by monitoring the dose and/or the use of analogs.

Regardless of the causes of immunosuppression, the ability of an agent to up-regulate the immune system would have profound consequences on improving host resistance against infection in both clinical and veterinary disease.

SUMMARY OF THE INVENTION

Accordingly, it is a purpose of the present invention to provide an agent for improving response of a mammalian immune system.

It is another purpose of the present invention to use DHEA subcutaneously or orally to improve the response of the mammalian immune system against viruses, such as CVB4, HSV2 or HIV.

DHEA, when administered by feeding or by subcutaneous injection significantly improves the host response to viral infection. The experimental animal data described herein shows that with infection (100,000 plaque forming units/animal) of a human coxsackievirus B4 strain, which causes mortality in about 90% of infected animals, mortality was reduced to 37% when animals were treated with DHEA. Moreover, DHEA induced an 80% elevation in the number of antibody forming cells, particularly in cells forming gamma globulin M (early antibodies), and gamma globulin G (secondary antibodies). This elevation in the number of antibody forming cells was evident only in DHEA treated and virus infected animals, but not in uninfected animals treated with DHEA, or in infected animals not treated with DHEA. In virus infected and DHEA-treated animals there was also an elevation in the number of monocyte cells, the particular white blood cells associated with a resistance to this infection. This elevation was not observed in DHEA-treated uninfected animals. This observation shows that this hormone can be used to up regulate the host immune response to virus infection, by increasing the number of antibody forming cells, elevating the number of white blood cells associated with resistance to virus infection and markedly reducing virus induced mortality. Moreover, virus (antigen) has to be present in order to demonstrate the up regulation of immunity by DHEA.

Other features and advantages of the present invention will be apparent from the following description taken in conjunction with the accompanying drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is a pair of graphs illustrating the effects of DHEA injection on the percent cumulative survival of C57BL/6J mice following virus infection.

FIG. 4 is a pair of graphs illustrating the effect of DHEA on the number of spleen antibody forming cells (AFC).

DETAILED DESCRIPTION OF THE PREFERRED EMBODIMENTS

Figure 1A:
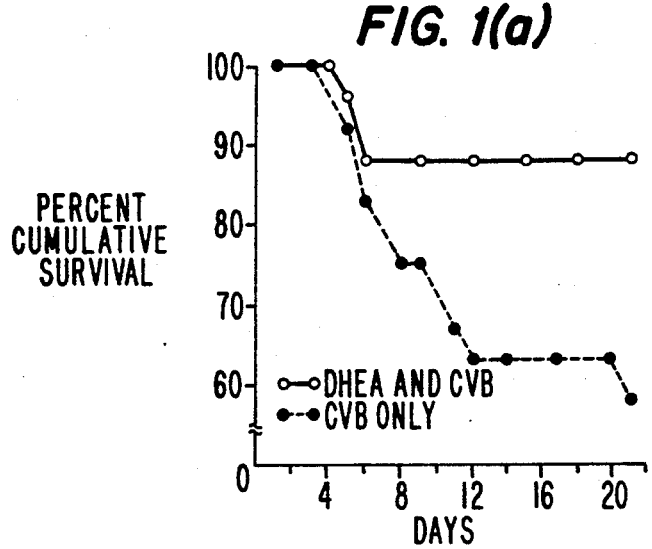
In FIG. 1(a) Male mice were injected intraperitoneally with CVB4, or with the virus and DHEA.

In general, the use of DHEA as described herein provides very high levels of protection against virus, Rickettsia, bacterial, fungal or opportunistic infections in immunocompromised animals and humans. These compositions may be used prophylactically to protect animals or patients from the consequences of infection by pathogenic organisms. In clinical medicine, this includes surgery patients, burn victims, cancer patients receiving chemotherapy, hypoplastic or aplastic anemias, or patients with diabetes. Up-regulation of immunity is of value in common dormitories as with military recruits, school, summer campers or disaster victims or with the aged in nursing homes subject to high infection risk.

DHEA is also of value in the treatment of immunocompromised AIDS victims or those infected with the HIV virus showing the AIDS related complex (ARC).

Another primary potential use includes veterinary medicine, animal populations during stressful shipping, mixing and early life adaptation periods or when subject to bacterial or virus infection that compromises immune response.

The present invention does not involve vaccine or antibiotic effects. Rather DHEA acts by producing a generalized and nonspecific immunological response on the part of the host, that manifests itself during infection. The invention does include acceptable carriers, diluents, vehicles and the like for systemic administration by feeding.

More particularly, previous studies have shown that diabetic mutation db+/db+ is associated with an impaired immune response in the inbred C57BL/KsJ mouse, and this host is markedly more susceptible to coxsackievirus B4 (CVB4) infection. R. M. Loria et al., Diab. Res. & Clin. Prac. 2, 91–96 (1986); L. B. Montgomery and R. M. Loria, J. Med. Virol. 19, 255–268 (1986). It is now recognized that diabetes mellitus in humans may be a virus mediated autoimmune reaction, which may result in the destruction of the Islet of Langerhans. H. Markholst and A. Lermark, in: Virus Infections and Diabetes Mellitus, Y. Becker ed. (Martinus Nijhoff Pub. Boston, 1987) pp. 111–124; and G. F. Bottazzo et al. in: The Diabetes Annual, 2, K. G. M. M. Alberti and L. P. Krall eds. (Amsterdam. Elsevier Publ. 1986) pp. 13–29.

Dietary DHEA has been reported to have an antidiabetic effect in the diabetic mutant mouse, D. L. Coleman et al., Diabetologia 31, 830–833 (1984); D. L. Coleman et al., Diabetes 33, 26–32 (1984); D. L. Coleman et al., Endocrinologia 115, 238–248 (1984): and D. L. Coleman, Endocrinologia 117, 2279–2283 (1985). The present inventors sought to determine whether the antidiabetic effect of DHEA could be mediated in part by an effect on the immune response and/or on the pathogenicity of the enterovirus CVB4.

Two acute virus infection models, with distinct replicative (RNA/DNA) and pathogenic mechanisms were examined to determine the effects of DHEA on virus-mediated pathophysiology. As a result of these studies, it was concluded peroral and subcutaneous administration of DHEA up-regulates the host immune system and reduces the virulence of RNA or DNA viruses that are lethal by widely different mechanisms.

Two different human virus isolates were used to challenge C57BL/6J inbred mice: one was the coxsackievirus B4 (CVB4) Edwards strain and the second was herpes simplex type 2 (HSV2). The former virus is lethal in mice, causes upper respiratory infection in humans and may play a role in juvenile diabetes. The latter virus causes skin disease.

Details on the passage history of CVB4 and tissue culture procedures are set out in R. M. Loria et al., Arch. Virology, 81, 251–262 (1984); R. M. Loria et al., Diab. Res. & Clin. Prac. 2, 91–96 (198); L. B. Montgomery and R. M. Loria, J. Med. Virol. 19, 255–268 (1986); R. M. Loria et al., J. Med. Virol. (1988). The HSV2 strain MS was obtained from the American Type Culture Collection (ATCC VR-540). This virus was grown and plaqued on Vero cells. For staining HSV2 plaques a 1% crystal violet was used for 20 minutes and then rinsed.

Male mice have been shown to be more susceptible than female mice to enterovirus infection and the reverse is true for HSV2 susceptibility. Compare S. Berkovich and M. Ressel, P.S.E.B.M. 119, 690–694 (1965) and S. Berkovich and M. Ressel, Archiv. Fur die Gesamte Virusforschung 22, 246–251 (1967), with S. C. Mogensen, Infection and Immunity 17, 268–273 (1977); D. A. Baker and S. A. Plotkin, P.S.E.B.M. 158, 131–134 (1978); and Yirrell, supra. Therefore male inbred C57BL/6J mice 6 to 8 weeks old (Jackson Laboratories, Bar Harbor, ME) were infected with CVB4, while female inbred mice of the same age and strain were used for HSV2 infections. The genetically immunodeficient hairless female HRS/J hr/hr inbred mice (Jackson Laboratories) at 6–8 weeks of age were used to test the effect of a functional immune system on the response to DHEA. H. J. Heiniger et al., Cancer Res. 34, 201–211 (1974); D. A. Johnson et al., Leukemia Res. 6, 711–720 (1982).

All animals were maintained on normal laboratory mouse chow (Agway RMH-3000, Agway, Syracuse, N.Y.). In experiments where animals were maintained on a semipurified diet high in animal fat, the diet contained 20% casein, 52.5 % sucrose, 18% animal fat (lard), 5% cellulose, 4% salts, 0.2% choline chloride, 0.1% inositol and 0.1% vitamin mix. Such a semipurified diet has been used extensively, R. M. Loria et al., Nutrition Reports Internat. 12, 509–518 (1976); R. M. Loria et al., J. Inf. Dis. 133, 655–662 (1976); A. E. Campbell et al., Atherosclerosis. 31, 295–306 (1978); A. E. Campbell et al., Infect. Immun. 37, 307–317 (1982).

Several routes of DHEA administration were examined. These included feeding as 0.4% of the diet, subcutaneous injection, or intraperitoneal injection. For injection, DHEA (Searle, Chicago Ill.) was suspended in 0.2 ml dimethyl sulfoxide (DMSO).

In CVB4 experiments, animals were infected with the virus 1 hour after DHEA injection, and each group was challenged (intraperitoneally) with a dose of CVB4 ranging from $10^2$ PFU/animal to $10^5$ PFU/animal. Four hours prior to viral infection animals were injected subcutaneously with 1 g/kg of DHEA. Control animals were injected with virus and 0.2 ml of DMSO.

The optimal dose of DHEA-mediating antiviral activity was determined by injecting animals with DHEA doses of 2 g, 1 g, 500 mg, and 250 mg/kg, respectively. Protection from lethal CVB4 and HSV2 injection was observed when DHEA was injected subcutaneously at a dose of 1 g/kg. Also, feeding DHEA at 0.4% concentration protected the animals from lethal virus infection. No significant protection from lethal virus infection was evident with any other subcutaneous dose of DHEA, or with any dose of the related steroid etiocholanolone, 3 $\alpha$-hydroxy-5.-androstan-17-one (Sigma Chemical Co., St. Louis, Mo.). In all subsequent experiments a dose of 1 g/kg DHEA subcutaneous (25 Mg/mouse) was used.

As previously described in Montgomery, supra, 10 days after CBV4 infection test animals were subjected to an intraperitoneal injection with 5X $10^8$ sheep red blood cells (SRBC), while control animals were immunized only with SRBC. Four days after SRBC immunization, animals were killed with an overdose of ether and the spleen removed. The procedure of E. Moller et al., Eur. J. Immunol. 3, 172–179 (1973), for the enumeration of spleen cells secreting IgM-antibody, was used in these experiments.

Peripheral white blood cells were counted following Diff-Quik (American Scientific Products, McGraw Park, Ill.) staining of blood smear. No differentiation of lymphocytes or monocytes by special stains or cell marker was done.

For histopathological studies animals were sacrificed by an overdose of methoxyflurane (Metofane, Pitman-Moore, Inc., Washington Crossing, N.J.), tissues were removed and fixed in phosphate-buffered formaldehyde at room temperature. Specimens were embedded in paraffin, sectioned and stained with hematoxylin and eosin.

The General Linear Models Procedure (SAS) was used to determine the significance of the particular changes in a given cell type. Whether there was a significant difference between the various groups was determined using Tukey's studentized range test for each variable at a $P \leq 0.05$ level. A confirmation of these results was obtained from the non parametric Wilcoxon Rank Sums test.

Figure 1B:
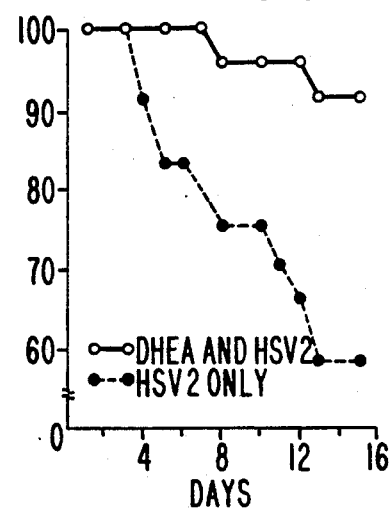
In FIG. 1(b) Female mice were injected intracraneally with HSV2, or with the virus and DHEA.

The effects of 25 mg DHEA injected subcutaneously on the percent survival following CVB4 and HSV-2 infection are presented in FIGS. 1a and 1b, respectively. The results show that the percent cumulative survival of animals following CVB4 infection was close to 90% in DHEA-treated mice as compared to about 58% in control animals ($P \leq 0.03$), (FIG. 1a). An almost identical increase in the percent cumulative survival was evident in HSV2-infected and DHEA-treated mice, 92% versus 58% in control HSV2-infected animals, (FIG. 1b).

Figure 2A:
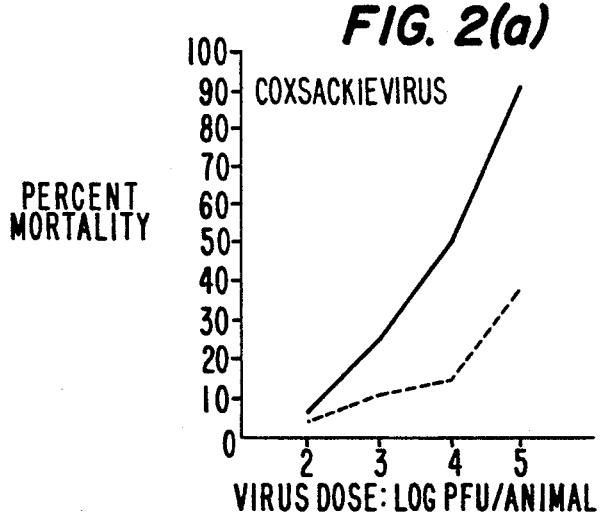
FIG. 2 is a pair of graphs illustrating the effects of DHEA injection on virus dose response of C57Bl/6J mice. X—X virus only; O—O virus and DHEA.
Figure 2B:
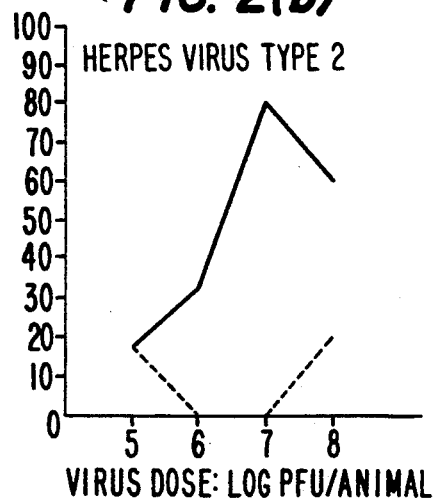
Figure 3:
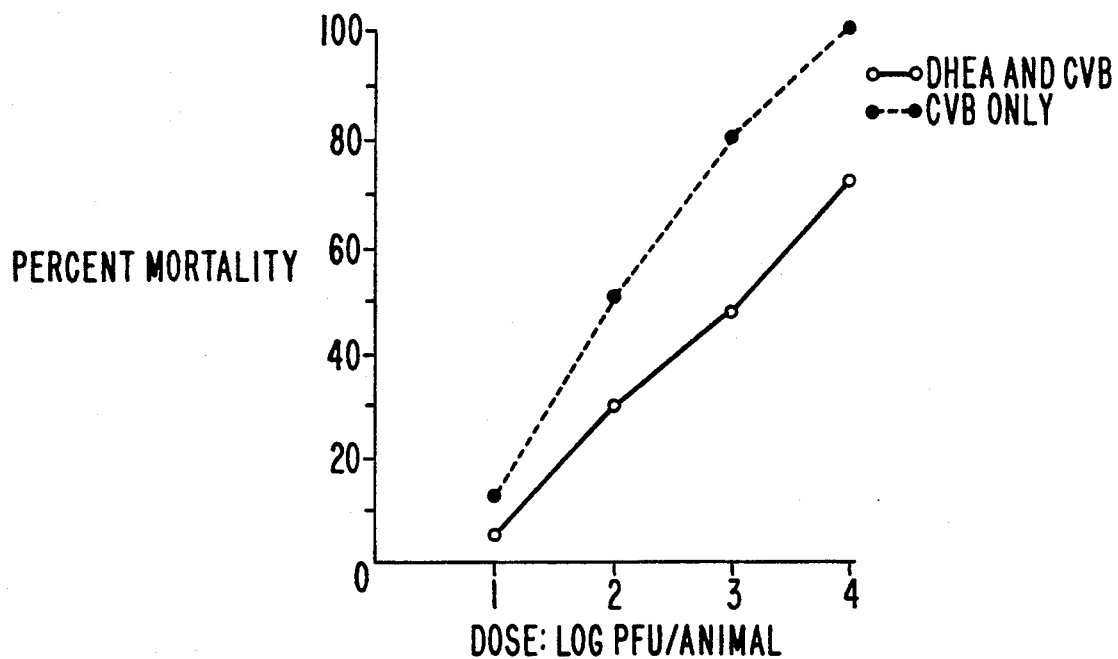
FIG. 3 is a graph illustrating the effects of feeding 0.4% DHEA on CVB4 dose response of C57BL/6J mice.

The effects of subcutaneous injected DHEA on virus-dose-dependent mortality following infection with CVB4 and HSV2 are presented in FIGS. 2a, 2b. The findings show that animals infected with CVB4 LD$_{100}$ dose ($10^5$ PFU /animal) had mortality reduced from 90% to 37.5% with DHEA treatment, while HSV2 induced mortality was reduced from 88% to 0 at a dose of $10^7$ pfu/animal. This protective effect of DHEA against intraperitoneal CVB4 and intracranial HSV2 infections was statistically significant, $P \leq 0.03$. These results confirmed that inbred C57Bl/6J mice fed 0.4% DHEA in a semipurified diet high in animal fat for 16 weeks prior to challenge was also associated with a significant resistance to CVB4 infection, $P \leq 0.05$ (FIG. 3).

In these experiments, we also tested the effects of the sulfated metabolite of DHEA, DHEAS, by subcutaneous or intraperitoneal injection as well as the effects of etiocholanolone at the above mentioned doses. There was no evidence of protection against virus lethality with either DHEAS or etiocholanolone.

Figure 4A:
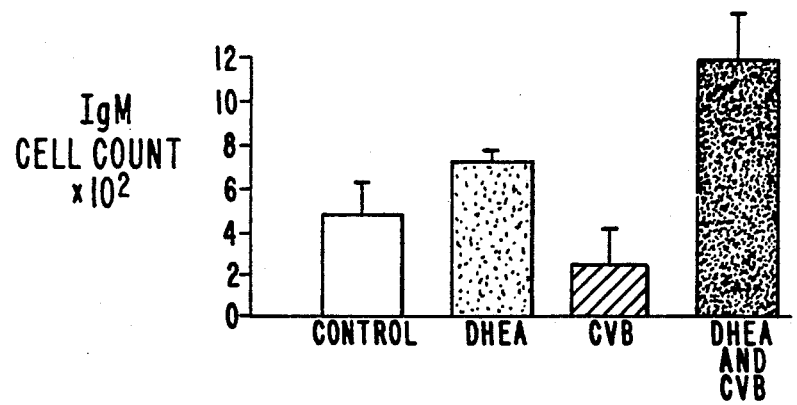
In FIG. 4(a) the number of spleen IgM AFC is compared.
Figure 4B:
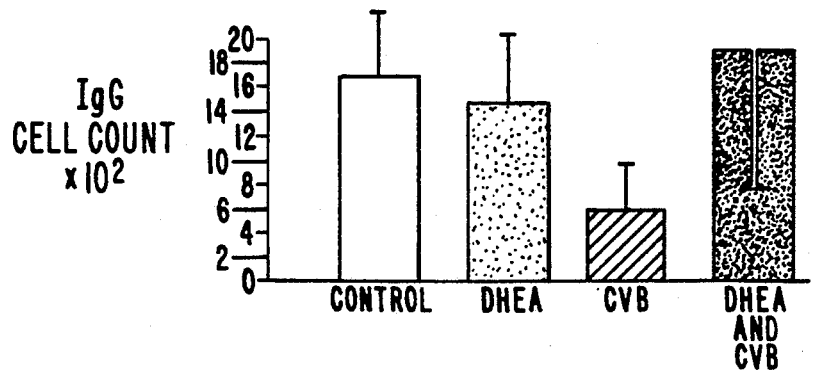
In FIG. 4(b) the number of spleen IgG AFC is compared.

The effect of DHEA on the number of spleen antibody forming cells (AFC) in virus-infected and uninfected animals was determined by sheep red cell immunization as described previously. The number of IgM AFC per $10^6$ spleen cells in uninfected and CVB4-infected mice with and without DHEA treatment are presented in FIG. 4a. As can be seen, the number of IgM AFC per $10^6$ spleen cells was 35% higher in uninfected DHEA-treated mice as compared to the uninfected control mice. This increase was not statistically significant. However, in CVB4-infected DHEA-treated mice the number of spleen IgM AFC was 80% higher than the number of IgM AFC in CVB4-infected control mice, $P \leq 0.025$. The number of spleen IgG AFC was also enumerated (FIG. 4b); in DHEA-treated/CVB4-infected mice a 70% increase in the number of IgG AFC was observed as compared to virus-infected mice not treated with DHEA. This increase however was not statistically significant.

Histopathological studies of hematoxylin and eosin stained spleen sections revealed that the spleen periarteriolar sheath of lymphocytes (PALS), which is composed largely of T lymphocytes that are primarily Thy 1.2 cells, were well developed in both DHEA-treated and in CVB4-infected animals. However, infection with CVB4 was associated with reduction in the number and size of spleen germinal centers. In contrast, in DHEA-treated animals, there was a marked increase in the number and size of splenic germinal centers suggesting B lymphocyte hyperplasia and a marked increase in the hematopoietic activity in the spleen red pulp. Furthermore, in untreated DVB4-infected animals, the spleen white pulp was characterized by a prominent "star" pattern indicative of phagocytosis of a large number of dead lymphocytes. J. G. Sinkovics et al., J. Inf. Dis. 120, 250–254 (1969); K. Sorger et al., Clin. Nephrol. 27, 111-24 (1987). In DHEA-treated/CVB4-infected animals, the "starry sky" pathological picture was reduced. These histological observations are suggestive of DHEA-mediated changes in the splenic lymphocyte and the hematopoietic cell populations.

The effect of DHEA on peripheral leukocyte concentrations was also evaluated in the following four groups: 1) control; 2) 1 g/kg DHEA subcutaneous; 3) CVB4-infected; and 4) 1 g/kg DHEA subcutaneous/CVB4-infected. All data were analyzed for statistical significance and the results are presented in the following Table 1.

TABLE 1

Effects of DHEA and Virus Infection on Peripheral Leukocytes Counts*

| Treatment | Day | Total Leukocytes | Monocytes | Neutrophiles | N |
|---|---|---|---|---|---|
| None | −1 | 11.20 ± 0.74 | 0.55 ± 0.13 | 1.04 ± 0.17 | 10 |
| Control | 3 | 11.30$^a$ ± 1.87 | 0.84 ± 0.27 | 0.64 ± 0.16 | 3 |
| DHEA | 3 | 8.37 ± 1.04 | 0.58 ± 0.07 | 0.74 ± 0.12 | 6 |
| CVB4 | 3 | 7.98 ± 0.53 | 0.42$^c$ ± 0.08 | 3.94$^c$ ± 1.00 | 4 |
| DHEA + CVB4 | 3 | 3.94$^b$ ± 0.88 | 0.13$^c$,d ± 0.02 | 2.60$^b$ ± 0.30 | 12 |
| Control | 7 | 10.30 ± 1.84 | 0.58 ± 0.22 | 0.94 ± 0.33 | 3 |
| DHEA | 7 | 12.30 ± 1.30 | 0.94 ± 0.11 | 1.40 ± 0.25 | 6 |
| CVB4 | 7 | 5.08 ± 1.32 | 0.44 ± 0.16 | 1.44 ± 0.46 | 6 |
| DHEA + CVB4 | 7 | 8.13 ± 0.61 | 1.38$^c$ ± 0.29 | 2.16$^d$ ± 0.29 | 12 |
| Control | 14 | 9.73 ± 0.49 | 0.31 ± 0.14 | 0.73 ± 0.21 | 3 |
| DHEA | 14 | 14.20 ± 1.92 | 0.50 ± 0.22 | 1.84 ± 0.17 | 5 |
| CVB4 | 14 | 11.10 ± 2.35 | 0.67 ± 0.41 | 4.95 ± 2.43 | 2 |
| DHEA + CVB4 | 14 | 14.00 ± 1.50 | 0.87 ± 0.15 | 4.73 ± 1.12 | 7 |

*All values are mean cells count × 10$^3$/mm$^3$ blood ± S.E.
$^a$Control animals were injected with both vehicle and medium at respective sites. Based on analysis of variance (ANOVA) the overall change on the third day was statistically significantly different for the total leukocyte, monocyte, and neutrophils counts at P ≦ 0.002, P ≦ 0.001 and 0.0003, respectively. On day 7, the change in monocytes counted were statistically significant, P ≦ 0.02. Tukey's studentized range test for multiple comparison at a level of P ≦ 0.05 was used to determine whether the difference between the particular groups was significant.
$^b$Different from uninfected control and DHEA-treated groups.
$^c$Different from uninfected control.
$^d$Different from DHEA-treated uninfected group.
$^e$Different from CVB4-infected group.

There was no significant effect of DHEA alone on the total leukocyte count as compared to untreated animals. However, the total leukocyte count 3 days after infection was significantly lower in the DHEA-treated/CVB4-infected animals, as compared to uninfected control or DHEA injected controls, P≦0.05. There were no significant differences in the total leukocyte counts between any of the experimental groups at subsequent sampling. Three days after CVB4 infection only, or in the DHEA-treated CVB4-infected group, the monocyte counts were 50% and 84.5% lower than the control group, respectively, P≦0.05. In contrast, 7 days after infection the monocyte counts of the DHEA-treated CVB4-infected group were 214% higher than the monocyte counts in the group infected with CVB4 that did not receive DHEA, P≦0.05. DHEA injection alone without CVB4 infection resulted in a 62% elevation of monocyte counts over control animals. There was no significant difference in the monocyte counts between the CVB4-infected animals not receiving DHEA and uninfected controls.

A biphasic response in peripherally sampled polymorphonuclear leukocyte (PMN) numbers was evident in DVB4-infected animals. Three days after infection the PMN counts reached 3.94×10$^3$ cells/mm$^3$, which was 515% higher than the PMN count in the control group of 0.64×10$^3$ cell/mm$^3$, P≦0.05. A second elevation in PMN counts was seen at 14 days in CVB4-infected or DHEA-treated CVB4-infected animals only. This elevation was not quite as accentuated and not statistically significant. In noninfected DHEA-treated animals no real change was noted in the number of PMNs.

The hairless mutation (hr/hr) in the inbred HRS/J mouse is associated with hereditary immunodeficiency and leukemogenesis (Heiniger, supra; Johnson, supra, and K. Holmes et al., Fed. Am. Soc. Exp. Biol. 82 3333 (1982). Experiments were done to test whether subcutaneous DHEA injection could affect the resistance of this strain to CVB4 infection. Inbred HRS/J hr/hr mice were injected subcutaneously with 1 g/kg DHEA and challenged intraperitoneally with 10$^5$ pfu/animal of CVB4 1 hour later. In contrast to the immunologically normal inbred C57BL/6J mice, DHEA did not protect this immunodeficient mutant from CVB4 lethality.

In contrast to protective subcutaneous DHEA injection the initial results show that DHEA given by the intraperitoneal route was not associated with host protection from virus induced mortality or up-regulation of the immune response. It was observed that subcutaneous injection of DHEA is associated with the formation of a local deposit leading to probably prolonged DHEA interaction with the lymphoid system. Prolonged feeding of 0.4% DHEA was also protective in the CVB4 model (FIG. 3). However, it is of particular interest to note that the magnitude and the range of protection against lethal virus infection associated with subcutaneous injection of DHEA was considerably greater than when DHEA was fed in the diet.

In vitro experiments were also done to determine whether DHEA had any direct effect on CVB4 infectivity and replication. HeLa cells in culture were incubated with either 2 μM or 20 μM DHEA and inoculated with 100 pfu of CVB4. No evidence of a reduction in the number of CVB4 plaque forming units could be detected at these concentrations of DHEA.

It is believed the protection against viral lethality seen with a single subcutaneous injection of DHEA (but not DHEAS) is attributed to an effect upon the host resistance and/or the immune system rather than upon the viruses per se. This supposition is supported by the observations that: 1) DHEA failed to influence CVB4 replication in vitro, where immune mechanisms are not present; 2) DHEA was ineffective in the inbred HRS/J hr/hr mouse which is genetically immunodeficient; 3) up-regulation of the immune response by DHEA was seen in CVB4-infected mice with regard to the number of spleen IgM and IgG AFC (FIG. 4); 4) administration of DHEA alone was also associated with enlargement of the spleen germinal centers which suggests stimulation of the lymphocyte dependent areas; 5) DHEA treatment of CVB4-infected animals resulted in a reduction of the "starry sky pattern", an indicator of cell killing, which was prominent in the spleens of CVB4-infected mice not treated with DHEA; and 6) finally, an increase in circulating mononuclear cells was observed in DHEA-treated/CVB4-infected mice which is consistent with the role of these cells in host defense against CVB4 infection, J. P. Woodruff, J. Immunol. 123, 31–36 (1979), as does the DHEA mediated decline in the splenic "starry sky" pattern.

The results of this study, then, demonstrate that DHEA, a native adrenal steroid hormone, which has been thought to be primarily an intermediary in testosterone and estradiol metabolism, J. B. Tyrell and P. H. Forsham, in: Basic and Clinical Endocrinology, F. S. Greespan and P. H. Forsham, eds. (Los Altos California, Lange Medical Publications 1983) pp. 258–294), can prevent mortality normally seen with at least two distant classes of viruses.

The virus responsible for AIDS can also be effected by DHEA up regulation of the immune system. AIDS is a disease characterized by loss of cell-mediated immunity and the development of frequent and eventually fatal opportunistic infections. The use of the term HIV embraces the retrovirus HIV-1 or HIV-2 (Human Immunodeficiency Virus Type 1 and Human Immunodeficiency Virus Type 2), which was discovered in 1983. HIV attacks and reduces the numbers of a subset of white blood cells, T lymphocytes. Expressed on the cell surfaces of these T lymphocytes is a molecule known as CD4 (such cells are also known as T4 cells). Such lymphocytes, most of which are included in what is functionally defined as the helper/inducer subset, constitute the major proportion of mature T cells. Another major subset of T cells expresses the CD8 molecule on their cell surfaces (such cells are also known as T8 cells). Most of these are classified as suppressor/cytotoxic cells. Normally the T4/T8 ratio is 1.5 to 2.0. In AIDS patients, however, this ratio is inverted due to a decrease in the absolute numbers of T4 cells, with normal numbers of T8 cells usually being preserved.

T4 cells specifically recognize and proliferate in response to antigens that they encounter in the body, at the same time releasing a variety of proteins known as lymphokines that regulate other immune system cells. Upon signaling by T4 cells, B lymphocyte cells recognize antigens and secrete specific antibodies to neutralize or eliminate antigenic bacteria and viruses as they travel through body fluids between cells. Similarly, following signaling from T4 cells, T8 cells become activated to kill other cells infected with intracellular pathogens. Furthermore, T4 cells modulate the activities of immune system cells known as natural killer cells and macrophages, which are involved in response to infection and perhaps to incipient malignancies.

A critical and early event in HIV infection involves the virus' attachment, via its envelope glycoprotein, to a receptor on the surface of a susceptible T4 cell, the CD4 molecule. The CD4 molecule at the T4 cell surface appears to distinguish potential target cells from HIV and to act as the receptor molecule that binds the virus and allows infection and subsequent viral replication as well as the cytopathic consequences of viral infection.

The immunodeficiency of AIDS clearly demonstrates the importance of T4 lymphocytes. Because of the loss of these cells, the remaining T lymphocytes from AIDS patients have diminished or, absent responses to antigens, and show subnormal production of essential immuno-regulatory factors. Due to their decreased numbers and functional capacity, T4 cells are unable to fulfill their necessary role in providing direction for the maturation of B cells and cytotoxic T cells. The ability of AIDS patients to mount antibody reactions to new antigens is severely compromised.

While an antiviral agent which could kill all infecting HIV or completely inhibit its replication (and at the same time have an acceptable toxicity profile) is clearly desirable, the situation is that no such agent is at present available. It would be even more desirable to be able to up-regulate the immune system to prevent the HIV virus, and other viruses, from expressing themselves. DHEA is just such an up regulator.

The potential value of DHEA in the treatment of AIDS disease is seen in the observation that the rate of cortisol catabolism by lymphocytes was indicative of their sensitivity to lysis by cortisol and that plasma from HIV, AIDS or AIDS complex infected patients has the capacity to inhibit cortisol catabolism resulting in increased lympholysis. Lymphocyte destruction by cortisol is enhanced in AIDS related disease and the DHEA protection of stress or corticosterone induced thymic lysis suggests DHEA would be of value in maintaining lymphocyte function or numbers in AIDS victims or related stress mediated viral disease.

DHEA is indicated for the treatment of AIDS and other viral infections that require up regulation of the immune response for the following reasons: DHEA is metabolizable (it is already present in the body as a natural component); it does not pose a serious toxic problem at levels known to be safe; it is chemically stable and relatively inexpensive; and there is wide clinical experience with DHEA.

Retrovirus infection from which the AIDS syndrome is derived has been immunologically linked to immunodeficiency in hosts as varied as poultry, mice and man. These agents effect the broad spectrum of immune response including antibody production and responsiveness, immunologic maturation, delayed hypersensitivity, graft rejection and T cell cytotoxic responsiveness, as discussed above. Similarly, other acute virus infections also have an immunosuppressive effect. The value of DHEA is reflected in the rise in IgM in $CB_4$ infection on DHEA treatment as well as the increase in monocytes induced by DHEA treatment in mice.

It is known that coxsackieviruses reduce the broad immune response to infection which enhances susceptibility to other infecting organisms. This was due to both a direct and indirect host effect of virus infection on the immunoregulating system. The end result is a syndrome in mice that bears some relationship to what is seen in AIDS infection in man. The effect of DHEA treatment on relieving the lethal pathology of $CB_4$ infection in mice; its stimulus to IgM production despite $CB_4$ infection and immunodepression led to testing its activity with victims of AIDS.

Two individuals diagnosed to have AIDS were treated with oral doses of DHEA and improved dramatically. A summary of the results follows.

Case 1: 28 year old caucasian male, active homosexual with AIDS Related Complex (ARC). Had affair with man who died of AIDS. History of "recreational" drug use (LSD, tranquilizers, speed, marihuana, cocaine, quaaludes and nitrous oxide). Heavy use of cocaine and alcohol up to 6/86. Was well till 1/86 when he developed "cold sores in his mouth" followed by fever and diarrhea.

Diagnosis: 28 year old caucasian male with fever of 103° F., anorexia (lack of appetite), malaise cough, and exertional dyspnea (shortness of breath). Chest X ray suggestive of Pneumocystis Carinii Pneumonia. Laboratory findings: HTLVIII positive, Pneumocystis Carinii culture positive, severe thrombocytopenia.

Diagnosis: Acquired Immune Deficiency Syndrome, with Pneumocystis Carinii Pneumonia, and secondary oral infection with Candida.

Started oral treatment of 400 mg/day of DHEA on Nov. 11, 1986. On Feb. 08, 1987 had gained 14 pounds, and was doing very well. Had severe toxic reaction to AZT, which was discontinued. Remained on DHEA as of May 23, 1987. Has been stable.

Case 2: White male with factor VIII deficiency hemophilia, was found HTLVIII positive 18 months previously. The Acquired Immune deficiency disease manifested as a "hepatitis" (inflammation of the liver) and lymphadenopathy (swelling of the lymph nodes). The number of T4 lymphocytes was low, and DHEA levels were normal.

Treatment: 40 mg/kg in 4 oral doses per day. The swollen lymph nodes (lymphadenopathy) promptly and dramatically decreased, appetite returned, gained weight and felt well. Presently stable.

Thus, the invention provides a pharmaceutical formulation for use in the prophylaxis and therapy of a viral infection or a complication or consequence thereof, comprising a prophylactically or therapeutically effective amount of DHEA as an active ingredient.

The pharmaceutical formulation according to the invention may be administered locally or systemically. Preferably administration is oral or by injection.

Suitable formulations for oral administration include hard or soft gelatin capsules, dragees, pills, tablets, including coated tablets, elixirs, suspensions, syrups or inhalations and controlled release forms thereof. DHEA may also be administered in the form of an infusion solution or as a nasal inhalation or spray.

Solid dosage forms, in addition to those formulated for oral administration, include rectal suppositories.

Suitable injectable solutions include subcutaneous, intracranial and intramuscular.

DHEA may also be administered in the form of an implant or formulated for transdermal administration, for example, in the form of transdermal patches.

Further, the invention provides the use of DHEA in the manufacture of a medicament for use in the prophylaxis or therapy of a viral infection, or a complication or consequence thereof.

The invention also provides a method for treating a viral infection in a mammal, comprising administering a therapeutically effective amount of a pharmaceutical formulation comprising DHEA to said mammal.

The invention further provides a method for the prophylaxis of a viral infection in a mammal comprising administering a prophylactically effective amount of a pharmaceutical formulation comprising DHEA to said mammal.

According to a further aspect of the invention there is provided a method for the prophylaxis and therapy of Acquired Immunodeficiency Syndrome (AIDS) in a patient, which comprises administering to said patient a prophylactically or therapeutically effective amount of DHEA or a pharmaceutical formulation containing it.

According to a still further aspect of the invention there is provided a method for the prophylaxis and therapy of Acquired Immunodeficiency Syndrome Related Complex (ARC) in a patient, which comprises administering to said patient a prophylactically or therapeutically effective amount of DHEA or a pharmaceutical formulation containing it.

DHEA may also be used concomitantly or in combination with an immune system booster or immunomodulator as an agent in the prophylaxis and therapy of a viral infection, or a complication or consequence thereof.

DHEA and the immunomodulator may be combined in a single dosage form or in discrete dosage forms.

Suitable immune system boosters or immunomodulators for use in accordance with the invention are selected from ABPP (Bropirimine); Ampligen (mismatched RNA) developed by Du Pont/HEM Research; anti-human α-interferon antibody manufactured by Advance Biotherapy and Concepts; anti-AIDS antibody (Nisshon Food); AS-101 (heavy metal based immunostimulant); ascorbic acid and derivatives thereof; β-interferon; Carrosyn (polymannoacetate); Ciamexon manufactured by Boehringer Mannheim; Cyclosporin; Cimetidine; CL246,738 manufactured by American Cyanamid; colony stimulating factor (CM-CSF) manufactured by Sandoz and Genetics Institute; α-interferon; γ-interferon; glucan; Hyperimmue (gamma-globulin) manufactured by Bayer; IMREG-1 (leucocyte dialyzate) and IMREG-2 manufactured by IMREG; immuthiol (sodium diethylthiocabarmate) manufactured by Institut Merieux; Interleukin-1, Interleukin-2 manufactured by Cetus Corporation, Hoffmann-La Roche and Immunex; isoprinosine (inosine pranobex); Krestin manufactured by Sankyo; LC-9018 developed by Yakult; Lentinan manufactured by Ajinomoto/Yamanouchi; LF-1695 manufactured by Fournier; MET-ENK (methionine-enkephalin) manufactured by TNI Pharmaceuticals and Sygma Chemicals; Minophagen C; MTP-PE (muramyl tripeptide) manufactured by Ciba-Geigy; Trexan (Naltrexone) manufactured by Du Pont; Neutropin; RNA immunomodulator developed by Nippon Shingaku; Shosaikoto and ginseng; thymic humoral factor; TP-5 (Thymopentin) manufactured by Ortho Pharmaceuticals; Thymosin fraction 5 and Thymosin 1; Thymostimulin; TNF (tumor necrosis factor) manufactured by Genentech; and vitamin B preparations.

The majority of the above-mentioned immunomodulators are administered orally.

Accordingly, the invention also provides a pharmaceutical formulation comprising DHEA together with an effective amount of an immune system booster or immunomodulator.

The invention further provides DHEA for use concomitantly or in combination with an antiviral agent in the prophylaxis and therapy of a viral infection, or a complication or consequence thereof.

DHEA and the antiviral agent may be combined in a single dosage form or in discrete dosage forms.

Suitable antiviral agents include: AL-721 (lipid mixture) manufactured by Ethigen Corporation and Matrix Research Laboratories; Amphotericin B methyl ester; Ampligen (mismatched RNA) developed by Du Pont/HEM Research; anti-AIDS antibody (Nisshon Food); AS-101 (heavy metal based immunostimulant); AZT (azidothymidine/Retrovir/Zidovudine) manufactured by Burroughs Wellcome; Betaseron (β-interferon) manufactured by Triton Biosciences (Shell Oil); butylated hydroxytoluene; Carrosyn (polymannoacetate) Castanospermine; Contracan (stearic acid derivative); Creme Pharmatex (Contains benzalkonium chloride) manufactured by Pharmelac; CS-87 (5-unsubstituted derivative of Zidovudine); Cytovene (ganciclovir) manufactured by Syntex Corporation; DDC (dideoxycytidine) manufactured by Hoffmann-La Roche and other nucleoside analogues; dextran sulphate; D-penicillamine (3-mercapto-D-valine) manufactured by Carter-Wallace and Degussa Pharmaceutical; Foscarnet (trisodium phosphonoformate) manufactured by Astra AB; fusidic acid manufactured by Leo Lovens; glycyrrhizin (a constituent of liquorice root); HPA-23 (ammonium-21-tungsto-9-antimonate) manufactured by Rhone-Poulenc Sante; human immunevirus antiviral developed by Porton Products International; Ornidyl (eflornithine) manufactured by Merrell Dow; Nonoxinol; pentamidine isethionate (PENTAM 300) manufactured by Lypho Med; Peptide T (octapeptide sequence) manufactured by Peninsula Laboratories; Phenytoin marketed by Park-Davis (Warner-Lambert Company); Ribavirin; Rifabutin (ansamycin) manufactured by Adria Laboratories; rsT4 (recombinant soluble T4) manufactured by Biogen, Genentech and Smith Kline & French; Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; Wellferon (α-interferon) manufactured by Burroughs Wellcome; and Zovirex (acyclovir) manufactured by Burroughs Wellcome.

It will be observed the above mentioned antiviral agents include some of the agents hereinbefore specified for use as immunomodulators together with DHEA in accordance with the invention. Isoprinosine, for example, is known to act as an immunomodulator but also has antiviral properties. The term "antiviral" as used in the present Specification also includes agents which interfere with the entry of viruses into a cell.

The invention also provides DHEA for use concomitantly or in combination with a drug useful in the prophylaxis and therapy of AIDS-associated opportunistic infections.

Although not wishing to be bound by any theoretical explanation of the invention, and while these studies do not reveal the specific effect(s) of DHEA on the immune system, it is believed that DHEA may interfere with the immunosuppressive action of glucocorticoids such as corticosterone. V. Riley Science 212, 1100–1109 (1983). More particularly, mice subjected to "rotation stress" experienced increased serum corticosteroid levels and developed thymic involution and reduced resistance to transplantable tumors. These involutional effects of stress were antagonized by the subcutaneous injection of 1 mg/animal of DHEA. V. Riley, in: M. J. Murdoch Foundation Report, Pacific Northwest Research Foundation (1982). In addition, DHEA also antagonized the effects of corticosterone injections on thymus involution.

Viral infections have been shown to cause an increase in glucocorticoid responses, E. M. Smith et al., Science 218, 1311–1312 (1982); A. J. Dunn et al., Science 238, 1423–1424 (1987); J. E. Blalock, Science 238, 1424–1425 (1987); J. B. Hammond and J. L. Rosenberg, J. of Lab. Clin. Med. 79, 814–823 (1972); D. Spackman and V. Riley, Proc. Am. Assoc. Cancer Res. 15, 143 (1974); G. A. Santisteban et al., P.S.E.B. Med. 139, 202–206 (1972), and thymic involution as well as a generalized immunosuppression, M. R. Escobar and P. D. Swenson, in: The Reticuloendothelial System; 4 Immunopthology, N. R. Rose and B. V. Siegel, eds. (New York, Plenum Press Publ. 1983) pp. 201–253; J. F. Woodruff and J. J. Woodruff in: Viral Immunology and Immunopathology. A. L. Notkins, ed. (Academic Press, New York 1975) pp. 393–418; B. Rager-Zisman and A. C. Allison, J. Gen. Virol. 19. 329–338; H. Y. Thong et al., Inf. & Immun. 12, 76–80 (1975). Thus it is reasonable to believe that DHEA or its metabolites act to protect the immune system from the stressful effects of the infection, i.e., glucocorticoid-mediated immune suppression, and thus enhance the ability of the host to control virus-mediated cytotoxicity, and possibly virus replication through various immune mechanisms. In this regard, a potent blocker of glucocorticoid synthesis, metyrapone, protects chickens against the lethal effects of Marek's disease, a herpesvirus-mediated lymphoproliferative disorder, and also protects mice against murine sarcoma virus, L. Thompson et al., Am. J. Vet. Research 41, 91–96 (1980); G. Rettura et al., J. National Cancer Institute 51, 1983–1985 (1973); B. L. Spangelo et al., Immunopharmacology 14, 11–20 (1987).

Presently, the effects of exogenous DHEA on glucocorticoid synthesis and action are unknown. Similarly, it is not known whether DHEA can antagonize glucocorticoid action on T lymphocytes or other lymphoid cells.

Since DHEA is considered to be a weak androgen, its host protective antiviral effect must be examined in the context of known sex hormone effect on the immune system. In particular, estradiol and progesterone have been reported to have effects on the natural killer cells. C. J. Grossman, Science 227, 257–260 (1985); M. Mohammad et al., Annals of Endocrinology 46, 415–419 (1985); I. Berci in: Pituitary Function and Immunity; I. Berci ed. (Boca Raton, Fla. CRC Press 1986) pp. 227–240. Thus DHEA, like other gonadal and pituitary hormones, could have independent regulatory effects on the immune response. D. R. Davila et al., Neuroscien. Res. 18, 108–116 (1987); D. H. Russell et al., J. Immunology 134, 3027–3031 (1985).

An alternative explanation for the sparing effect of DHEA in these acute viral infection models is that this steroid hormone may reduce virus-mediated T lymphocyte killing and reduce the number of anti-viral cytotoxic T cells, leading to a reduced tissue pathology. Indeed, cytotoxic T lymphocytes have a major role in the pathogenesis of CVB4 infection while humoral immunity is protective. Woodruff (1975, 1978), Escobar; Ragar-Zisman; and, Thong, supra. The opposite is seen in primary HSV infections (Lopez, Rouse, supra). Resistance is primarily mediated by T lymphocytes, while antibody protection is not as significant. The observation of an increased proliferation of the spleen germinal centers in DHEA-treated animals and the reduction in the viral killing of lymphocytes in DHEA-treated/CBB4-infected animals supports this hypothesis. Furthermore, the alteration of circulating leukocytes and the elevation in monocytes seen in DHEA-treated/CVB4-infected mice suggest a modulatory effect of DHEA on monocytes at various stages of the infection process. Monocytes have been reported to serve as effector cells in CVB4 infections, Woodruff (1979), supra, and it is possible that the changes in circulating monocyte levels reflect on the action of DHEA on tissue distribution or generation of these cells.

In these studies, anti-viral effects were observed only when DHEA was given subcutaneously or peroral, indicating that the route of DHEA administration may be a critical factor in the up-regulation of the host immune response. As is evident from FIGS. 2 and 3, the magnitude and the range of protection against lethal virus infection associated with subcutaneous injection of DHEA were considerably greater than when DHEA was fed in the diet. Recent reports show that the skin may have unique immune functions. C. A. Romerdahl and M. L. Kripke, Cancer and Metastasis Review 5, 167-178 (1986); J. W. Streilein and R. E. Tigelaar in: Photoimmunology, Parrish et al. eds. (Plenum Publishing, New York, 1983) pp. 95-130. Indeed the skin is known to contain a population of cutaneous immune cells, which include the epidermal Langerhans cells and keratinocytes that produce an epidermal thymocyte-activating factor, similar to IL-1, D. N. Sauder, Lymphokine Research 3, 145-151 (1984), in the murine system's the Thy-1+ dendritic epidermal cell. It has been suggested that the Thy-1+ cell has a role in immune surveillance. P. R. Bergstresser et al., J. Inv. Dermatol. 81, 286-288 (1983); E. Tschachler, et al., J. Invest, Dermatol. 81, 282-285 (1983). The Thy-1+ cell may also play a role in the presentation of antigen. S. Sullivan et al., J. Invest. Dermatol. 84, 491-495 (1985). Consequently, it is possible that the increase in resistance following subcutaneous DHEA injection is associated with activation of the skin particular immune functions.

The ability of DHEA to influence the immune system is also supported by the reports that DHEA and its bromo derivative have inhibited lymphoblastic transformation in human lymphocytes in vitro. In addition, DHEA has prevented the autoimmune lupus like syndrome in the NZB mouse that is thought by some to be caused by a slow virus (Henderson; Schwartz, supra).

Whatever the mechanism of DHEA's action in the acute viral models, these studies suggest that prolonged exposure to DHEA is also an important factor for obtaining the protective effect. Either prolonged feeding for 16 weeks or subcutaneous deposition of the hormone appeared to be required for achieving antiviral protection (FIG. 3), while intraperitoneal bolus administration did not protect the host against CVB4 infection. Furthermore, injection of DHEAS in the mouse, either subcutaneously or intraperitoneally, showed no antiviral action, suggesting that the protective action of DHEA is through a pathway independent of sulfation.

An unexpected finding in these studies was that the protection seen with DHEA was enhanced by increasing the virus dose in both infection models (FIGS. 2a, 2b). These results suggest that a certain critical virus load is required to activate the protective mechanism(s) induced by DHEA. This phenomenon could be mediated by the need for a certain amount of viral antigen to trigger the pertinent DHEA-modulated immunological process. Another possibility is that a threshold amount of virus might be required to activate the adrenal cortex if the protective DHEA effect should prove to be mediated through antagonis of glucocorticoids or other steroid effects.

The protective effect of subcutaneous DHEA injection against intracranial HSV2 (FIGS. 1 and 2), was obtained by injection of the hormone 4 hours prior to infection. However, does timing is critical, if injection of HSV2 intracranial and DHEA subcutaneously was 1 hour apart, no antiviral effect was produced. This observation suggests that either DHEA has to penetrate the blood-brain barrier to achieve its effect or the lag is necessary for DHEA to achieve up-regulation of the host immune system.

Our observations demonstrate that up modulation of the host immunity by DHEA is an effective approach for the treatment of viral infections. Specific agents to fight specific viruses are not needed. One does not have to worry about the treatment ultimately failing because the virus changed its characteristics. This approach also has significant advantages since it can be used with or without conventional antiviral chemotherapeutic treatments.

In summary, it can be seen from the above that dietary and subcutaneous administration of DHEA provides a new, effective approach to the treatment of both RNA and DNA viral infection; it may have broad clinical value where immunosuppression is a manifestation of infectious pathology or aging. DHEA, in contrast to clinical corticosteroids, is neither diabetogenic nor anti-inflammatory. Its benign clinical side effects (Regelson, Nestler, supra) suggest that it may have a place in the clinical treatment of viral infections where immunosuppression is an important concomitant of the infectious process.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

It is claimed:

1. A method for increasing a host mammalian immune system's response to infectious agents and immunogens, comprising the step of:
    administering to the host subcutaneously, transdermally, intradermally, orally or nasally, a prophylactically and therapeutically effective dose of dehydroepiandrosterone to up-regulate the host immune system against infection and immunogen, wherein the up-regulation results in a greater host resistance against infection and facilitation of the host immune system's response when exposed to the immunogen.

2. The method as recited in claim 1, wherein the infectious agents include viral, bacterial, fungal, parasitic, veroid and prion.

3. The method as recited in claim 2, wherein the viral infectious agent includes RNA viruses and DNA viruses.

4. The method as recited in claim 1, wherein the dose of dehydroepiandrosterone is in the range of 25 mg/kg to 2 g/kg of body weight of the mammal.

5. A method for increasing a host mammal's immune system responsive to viral infection, comprising the step of:

administering to the host subcutaneously, transdermally, intradermally, orally or nasally, a prophylactically and therapeutically effective dose of dehydroepiandrosterone to up-regulate the hose immune system against infection, wherein the up-regulation results in greater host resistance against infection when exposed to the agent.

6. The method as recited in claim 5, wherein the virus is an RNA or DNA selected from the group consisting of CVB4, H5V2 and HIV.

7. The method as recited in claim 5, wherein the dose of dehydroepiandrosterone is in the range of 25 mg/kg to 2 g/kg of body weight of the mammal.

* * * * *